United States Patent [19]

Webinger

[11] 4,340,168
[45] Jul. 20, 1982

[54] CARTON WITH LOCKING MECHANISM FOR SLIDABLE TOP AND BOTTOM

[75] Inventor: George Webinger, Robbinsdale, Minn.

[73] Assignee: Champion International Corporation, Stamford, Conn.

[21] Appl. No.: 199,581

[22] Filed: Oct. 22, 1980

Related U.S. Application Data

[63] Continuation-in-part of Ser. No. 102,898, Dec. 12, 1979, Pat. No. 4,277,014.

[51] Int. Cl.³ .......................... B65D 5/32; A61L 9/04
[52] U.S. Cl. .............................. 229/23 BT; 229/41 C; 229/11; 239/58; 205/0.5
[58] Field of Search .......... 229/416, 41 D, 43, 23 BT, 229/45 R, 34 R, 8, 45, 35, 5.5, 15, 34, DIG. 14, 9, 10, 11, 20; 206/626, 624; 220/87, 366; 239/58, 59, 60

[56] References Cited

U.S. PATENT DOCUMENTS

| | | | |
|---|---|---|---|
| 1,623,715 | 4/1927 | Berkowitz | 229/41 C |
| 2,412,402 | 12/1946 | Huye | 229/45 |
| 2,832,466 | 4/1958 | Sheard | 229/41 C |
| 3,003,676 | 10/1961 | De Nola | 229/35 |
| 3,115,292 | 12/1963 | Repking | 229/23 BT |
| 3,261,533 | 7/1966 | Repking | 229/41 C |
| 3,966,112 | 6/1976 | Gordon | 229/23 BT |
| 4,196,843 | 4/1980 | Garmon | 229/45 R |
| 4,215,783 | 8/1980 | Vanderlugt | 206/626 |
| 4,264,031 | 4/1981 | Goebel | 229/45 R |
| 4,289,240 | 9/1981 | Mueller | 206/624 |

*Primary Examiner*—William Price
*Assistant Examiner*—Gary E. Elkins
*Attorney, Agent, or Firm*—Evelyn M. Sommer

[57] ABSTRACT

A paperboard carton and blanks therefor formed from a top unit and a bottom unit which are relatively slidable. A locking mechanism prevents the units from being fully separated. This locking mechanism comprises a locking flap hingedly coupled to and folded against a side wall on either of the top and bottom units and a corresponding stop member formed on an opposed side wall of the other of the top and bottom units. The stop member is comprised of two side glue flaps extending integrally from two adjacent side walls, each having a tab extending therefrom. The tabs engage the distal end of the folded locking flap to prevent full separation. Advantageously, the locking flap is trapezoidal and the side glue flaps form a trapezoidal recess with the tabs forming the smaller base thereof. An air freshener material or insect poison can be located inside the carton.

4 Claims, 12 Drawing Figures

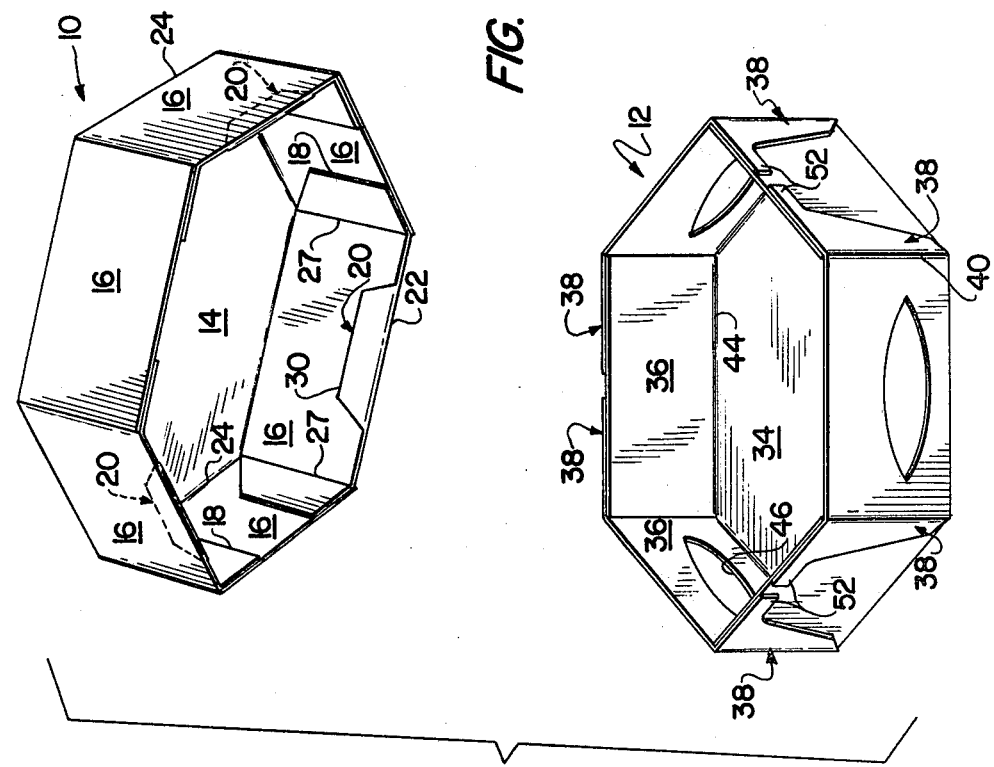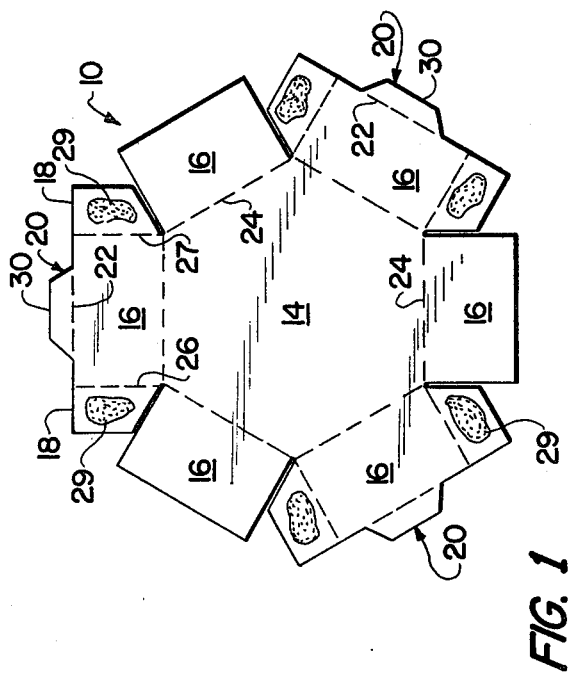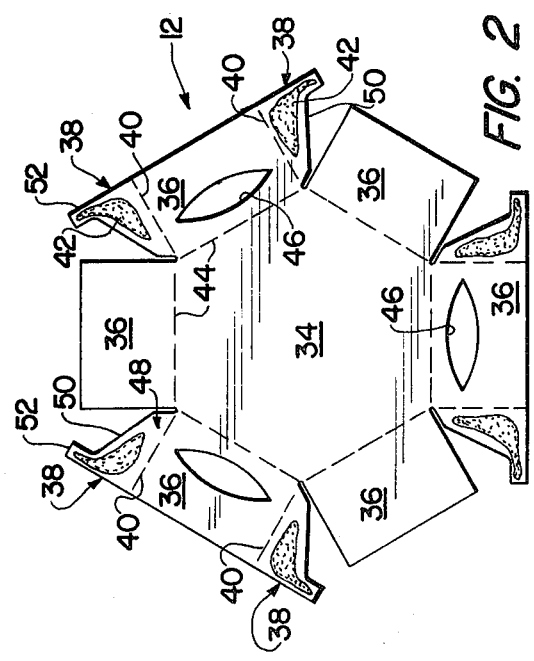

CARTON WITH LOCKING MECHANISM FOR SLIDABLE TOP AND BOTTOM

RELATED APPLICATION

This application is a continuation-in-part of my co-pending application Ser. No. 102,898, filed on Dec. 12, 1979, now U.S. Pat. No. 4,277,014 and entitled IMPROVED AIR FRESHENER.

FIELD OF THE INVENTION

The present invention relates to a paperboard carton and the blanks therefor formed from a top unit and a bottom unit which are relatively slidable. A locking mechanism prevents these units from being fully separated. An air freshener material or an insect poison can be located inside the carton.

BACKGROUND OF THE INVENTION

There are a variety of active materials for use in household and commercial applications including air fresheners and insecticides. These materials are usually packaged in solid form in containers having apertures to expose the material to ambient air. Frequently, products of this type are packaged in containers having a plurality of apertures which are closed at the time of purchase but which are opened at the time of use to allow air to circulate over the surface of the solid active material. In the case of an air freshener, the scent escapes from the container to freshen the room in which it is located. In the case of an insecticide, the scent attracts insects which can enter the container via the apertures and upon coming in contact with the insecticide are killed.

In one type of carton, the openings are covered with a panel of release paper. When the consumer is ready to use the product, the release paper is pealed from the face of the container to allow ambient air to circulate through the openings. In another type of carton, the consumer activates the air freshener material be squeezing to release an encapsulated active ingredient. In yet another type of carton, holes in an outer carton wall are opened or closed by a slidable inner sheet which acts as a valve.

Molded plastic containers, usually consisting of a molded shell and a separate molded cover, also have been employed to hold air freshener material. However, the cost of making them is very high. The shell and cover must be molded in separate operations and stored in unassembled form until the air freshener insert is loaded. The cover then must be glued or otherwise secured to the shell to provide a closed container. The extra time required for the separate manufacturing and assembly operations results in added manufacturing costs for the package and therefore ultimately for the product sold therein. In addition, the fact that the molded shells and covers must be shipped and stored in their molded form will also cause increased transportation and storage costs.

In a prior patent application, U.S. Ser. No. 25,012, filed Mar. 29, 1979, entitled "Carton With Adjustable Air Passages", assigned to the same Assignee as the present invention, an improved package for controllably releasing active materials to the air is disclosed which has inner and outer slidable members constructed of a sheet material wherein the inner and outer members can be slidably moved between fully opened and closed positions or positions intermediate thereof. The carton has a plurality of adjustable air passages and comprises: (a) a first tapered sleeve forming an outer carton unit, the first sleeve being closed at at least one end and having a plurality of spaced openings therein, and (b) a second tapered sleeve forming an inner carton unit, the second sleeve being nested within the first sleeve and being slidable between a first and a second position (or a position intermediate thereof), the second sleeve being closed at at least the end opposite the end closed in the first sleeve and having a plurality of spaced openings therein arranged complementally to spaced openings in the outer carton unit to align with the openings therein when the inner carton unit is in the first position, and to align with the spaces between the openings in the outer carton unit when the inner carton unit is in the second position. When opened or partially opened, the active material can be released to the air.

In the parent U.S. Pat. No. 4,277,014, entitled "Improved Air Freshener", assigned to the same Assignee as the present invention, an improved air freshener is disclosed which includes a regular, polygonal lower unit and a complementally shaped upper unit which are movable relative to each other along a common, longitudinal axis. The upper unit has a plurality of openings spaced about its top wall which are selectively opened by relative movement of the units away from each other to enable air to circulate through the openings to contact and diffuse an active air freshener material housed within the lower unit. The top of the lower unit has a plurality of triangularly shaped panels which cover the air freshener material and act with the plurality of openings in the upper unit to provide air passages to the air freshener material. The upper and lower units have a specific mechanism for precluding full axial separation of the upper and lower units when they are pulled in an opposite direction. This locking mechanism comprises a flap cut out of the triangular flaps in the bottom unit and folded outwardly and then downwardly and an inwardly bent and glued flange on the bottom of the side wall of the upper unit.

However, this type of locking mechanism requires a large amount of material, extensive cutting of the paperboard forming the carton and is not readily set up by machine.

U.S. Pat. No. 4,196,843 to Garmon issued on Apr. 8, 1980 and assigned to the same Assignee as the present invention, discloses a pair of telescoping upper and lower carton units precluded from full seperation by downwardly folded locking flaps on the lower unit and U-shaped cut-outs on the upper unit receiving the locking flaps. However, this locking mechanism also requires considerable material and extensive cutting and folding.

SUMMARY OF THE INVENTION

Accordingly, a primary object of the present invention is to provide a carton with a locking mechanism for a slidable top and bottom and blanks therefor which is readily set up by machines.

Another object of the present invention is to provide such a carton and blanks therefor which use a limited amount of material, cutting and folding during fabrication and set up.

Another object of the present invention is to provide such a carton and blanks therefor which can readily contain an air freshener or an insecticide in which relative slidable movement of top and bottom units exposes such materials to ambient air.

The foregoing objects are basically attained by providing a carton formed of paperboard comprising an upper unit including a regular polygonal top wall, and a plurality of side walls coupled to and extending downwardly from each edge of the top wall; a lower unit adapted to mate with and slide relative to the upper unit along a common longitudinal axis and including a regular polygonal bottom wall complemental in shape to the top wall, and a plurality of side walls coupled to and extending upwardly from each edge of the bottom wall, the side walls of the upper unit overlying the side walls of the lower unit and being slidable relative thereto; and means on said upper and lower units for precluding their separation in a direction along the longitudinal axis, the means including a plurality of locking flaps hingedly coupled to one of the upper and lower units at the distal longitudinal edge of a plurality of the side walls and folded thereagainst, and a plurality of stop members rigidly coupled to the other of the upper and lower units for engaging the distal edge of the locking flaps, each of the stop members comprising a pair of tabs extending across the side wall associated therewith.

A paperboard blank for forming the top unit of such a carton comprises a regular polygonal central panel; a rectangular panel hingedly coupled along a longitudinal edge thereof to each edge of the central panel; side flaps hingedly coupled to both lateral edges of alternate ones of the rectangular panels; and flaps hingedly coupled to alternate ones of the rectangular panels along the distal longitudinal edges of said rectangular panels, each of said flaps having a lateral dimension which is less than the lateral dimension of the rectangular panel to which it is coupled.

A paperboard blank for forming a bottom unit of such a carton comprises a regular polygonal central panel; a rectangular panel hingedly coupled along a longitudinal edge thereof to each edge of the central panel; and side flaps hingedly coupled along fold lines to both lateral edges of alternate ones of the rectangular panels, the side flaps each having a tab extending outwardly therefrom substantially perpendicular to the fold line thereof.

Other objects, advantages and salient features of the present invention will become apparent from the following detailed description, which, taken in conjunction with the annexed drawings, discloses preferred embodiments of the present invention.

DESCRIPTION OF THE DRAWINGS

Referring now to the drawings which form a part of this original disclosure:

FIG. 1 is a top plan view of the exterior surface of a blank in accordance with the present invention for forming the upper unit thereof;

FIG. 2 is a top plan view of the interior surface of a blank in accordance with the present invention for forming the lower unit thereof;

FIG. 3 is an exploded perspective view of the upper and lower units of the present invention constructed from the blanks of FIGS. 1 and 2 to form a carton;

DETAILED DESCRIPTION OF THE INVENTION

Figure 4:
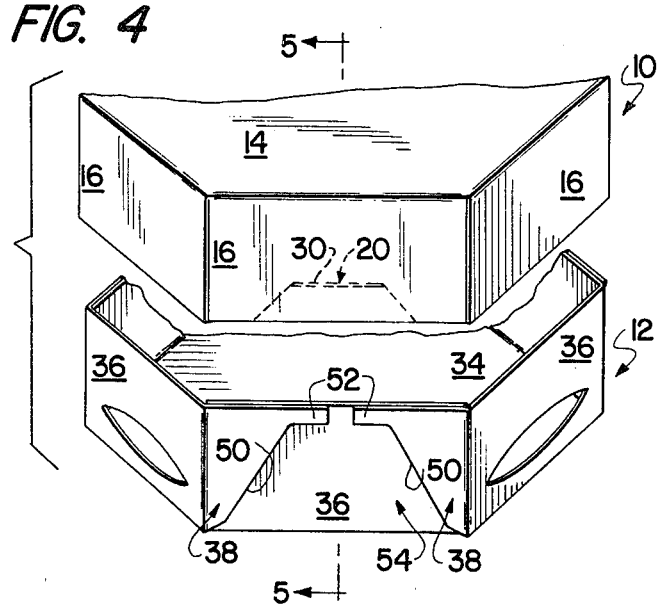
FIG. 4 is a fragmentary side elevational view of the upper and lower units aligned and about to be slid together.
Figure 5:
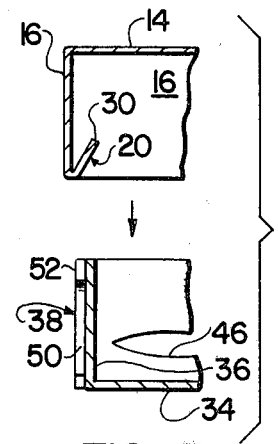
FIG. 5 is a sectional view taken along lines 5—5 in FIG. 4.
Figure 6:
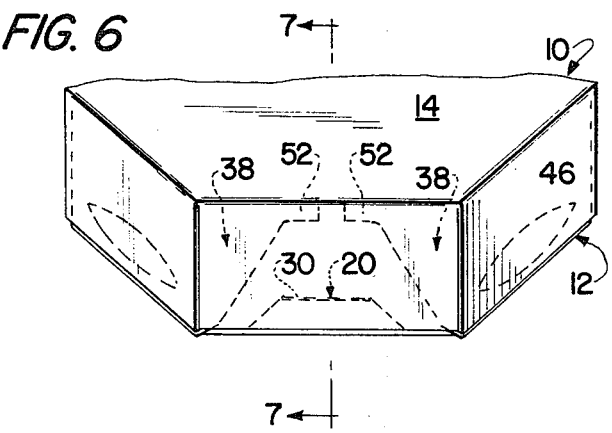
FIG. 6 is a fragmentary side elevational view of the upper and lower units with the upper unit receiving the lower unit therein.

Referring now in detail to FIGS. 1–9, a paperboard blank for an upper unit 10 in accordance with the present invention is shown in FIG. 1 and a paperboard blank for the lower unit 12 is shown in FIG. 2. These blanks can be set up as seen in FIG. 3 with the lower unit 12 being slidably engaged into the upper unit 10, as seen in FIG. 6. In the configuration shown in FIG. 3, the carton formed by the two units can have a solid material such as an insecticide inside the two units.

Referring now specifically to FIG. 1, the interior surface of the upper unit 10 is shown comprising a regular polygonal central panel or wall 14, a rectangular panel 16 hingedly coupled along a longitudinal edge thereof to each edge of the central panel 14, side flaps 18 hingedly coupled to both lateral edges of alternate ones of the rectangular panels 16 and locking flaps 20 hingedly coupled to alternate ones of the rectangular panels along the distal longitudinal edges thereof via fold lines 22. Each of the rectangular side panels 16 is hingedly coupled to the central panel along fold lines 24 and each of the side flaps is hingedly coupled to the lateral edges of the alternate ones of the rectangular panels along fold lines 26 and 27.

The side flaps 18 are in the nature of glue flaps having adhesive spots 29 on the interior surface thereof seen in FIG. 1. The regular polygonal central panel 14 is shown as a hexagon in FIG. 1; although it could be any desirable regular polygon.

The locking flaps 20 are isosceles trapezoids, the sides thereof having angles with fold line 22 of about 45°. The lateral dimension of the locking flaps 20 is less than the lateral dimension of the rectangular side panels 16 and the longitudinal dimension of the locking flaps is less than the longitudinal dimension of such side panels 16. The larger base of the trapezoidal locking flaps coincides with the fold line 22 and is thus hingedly coupled to the rectangular panel. Each of the locking flaps 20 has a substantially straight distal edge 30 which provides the locking characteristic thereto as will be described in more detail hereinafter.

In order to set up the upper unit 10 into the configuration shown in FIG. 3, the side panels 16 are folded along fold lines 24 inwardly as seen in FIG. 1 so that they are substantially perpendicular to central panel 14, which forms a top wall, these side panels 16 thereby forming side walls, the side flaps 18 with the adhesive 29 thereon being placed against the inside surface of the adjacent side panels 16. Then, in order to make the upper unit 10 ready for sliding over and telescopically receiving the lower unit 12, the locking flaps 20 are pivoted about fold lines 22 from the position shown in FIG. 1 through substantially 180° to the position shown in FIGS. 3 and 5 in which the locking flaps 20 are substantially against the interior surfaces of the side panels 16.

Referring now to FIG. 2, the lower unit 12 is shown comprising a central panel 34, a rectangular side panel 36 hingedly coupled along a longitudinal edge thereof to each edge of the central panel, and side flaps 38 hingedly and integrally coupled along fold lines 40 to both lateral edges of alternate ones of the rectangular panels. Each of the side flaps 38 are in the nature of glue flaps having adhesive spots 42 on the interior surface thereof, as seen in FIG. 2. Preferably, the adhesive extends over substantially all of the surface of the side flaps 38.

The rectangular side panels 36 are hingedly coupled to the central panel by means of fold lines 44 at the edges of the panel and on one of the longitudinal edges of each rectangular side panel.

Selected ones of the rectangular side panels 36 have openings 46 therein to allow air to pass therethrough.

Each of the side flaps 38 has a substantially right triangular base portion 48 which is hingedly coupled along fold line 40 to the rectangular side panel 36 and which has an outer edge 50 at an angle of less than 90° and advantageously of about 60° to the fold line 40. Extending outwardly from the base portion 48 is a substantially rectangular tab 52 which is substantially perpendicular to fold line 40.

In order to set up the lower unit 12 the rectangular side panels 36 are pivoted 90° from the position shown in FIG. 2 along fold lines 44 so that they are substantially perpendicular to central panel 34 and thereby form side walls, the central panel 34 forming a bottom wall. The side flaps 38 are also folded along fold lines 40 so that the adhesive 42 rigidly connects the side flaps 38 to the rectangular side panel 36 which is adjacent thereto. This is seen in FIG. 3 where two side flaps 38 are rigidly connected via adhesive 42 to the adjacent side panel 36, these side flaps 38 being integrally formed and extending from alternate and adjacent side panels 36.

Referring now to FIG. 4, as seen therein, the adjacent opposed side flaps 38 rigidly coupled to one of the side panels 36 define a trapezoidal recess 54 comprising the bottom sides of the two tabs 52, which are preferably parallel to the central panel 34, and the two facing outer edges 50 on the adjacent side flaps 38.

Figure 7:
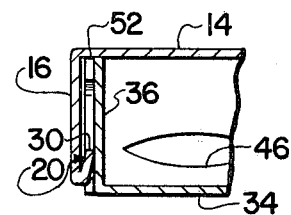
FIG. 7 is a sectional view taken along lines 7—7 in FIG. 6.

Once the upper unit 10 is aligned with the lower unit 12 so that each of the three folded-in locking flaps 20 is above a corresponding trapezoidal recess 54, and the material to be contained inside the carton formed by the two units is placed inside, the upper unit 10 is moved downwardly from a position shown in FIGS. 4 and 5 so that the side panels 16 slidably engage and receive therein the side panels 36 of the lower unit. This is shown in FIGS. 6 and 7 with the upper unit 10 resting on the lower unit 12 and the carton thereby formed being closed. The openings 46 are also closed-off by outer side panels 16. In this position, the locking flaps 20 because of the memory of the paperboard of which they are formed tend to spring away from the side panels 16 into a frictional engagement with the exterior surface of side panels 36 as best seen in FIG. 7. In moving from the position shown in FIGS. 4 and 5 to that shown in FIGS. 6 and 7, the inwardly folded locking flaps 20 slide over the tabs 52 at the top of the trapezoidal recess 54. In all events, in the position shown in FIGS. 6 and 7, the locking flaps 20 lie below the tabs 52 and against side panels 36 of the lower unit 12 in the trapezoidal recesses.

In order to selectively open the openings 46, the upper and lower units can be slidably moved relative to one another along their common longitudinal axis. They will tend to stay in the separated position to which they are pulled because of the frictional engagement of the locking flaps 20 against the exterior surfaces of the rectangular side panels 36.

Figure 8:
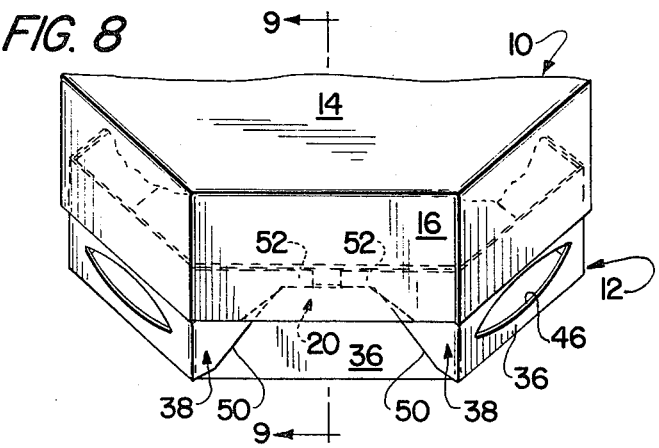
FIG. 8 is a side elevational view of the upper and lower units fully extended with the locking flap on the upper unit engaging the tabs on the lower unit precluding full separation therebetween.
Figure 9:
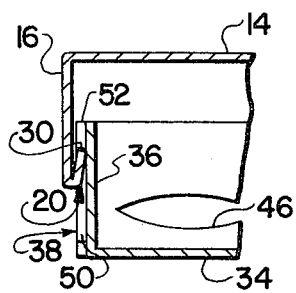
FIG. 9 is a sectional view taken along lines 9—9 in FIG. 8.

There is a limit to the relative movement therebetween and separation is precluded by engagement of the distal edge 30 on each locking flap 20 with the bottom of the tabs 52, as seen in FIGS. 8 and 9. In this position, the openings 46 are fully opened so that air can pass therethrough.

Figure 12:
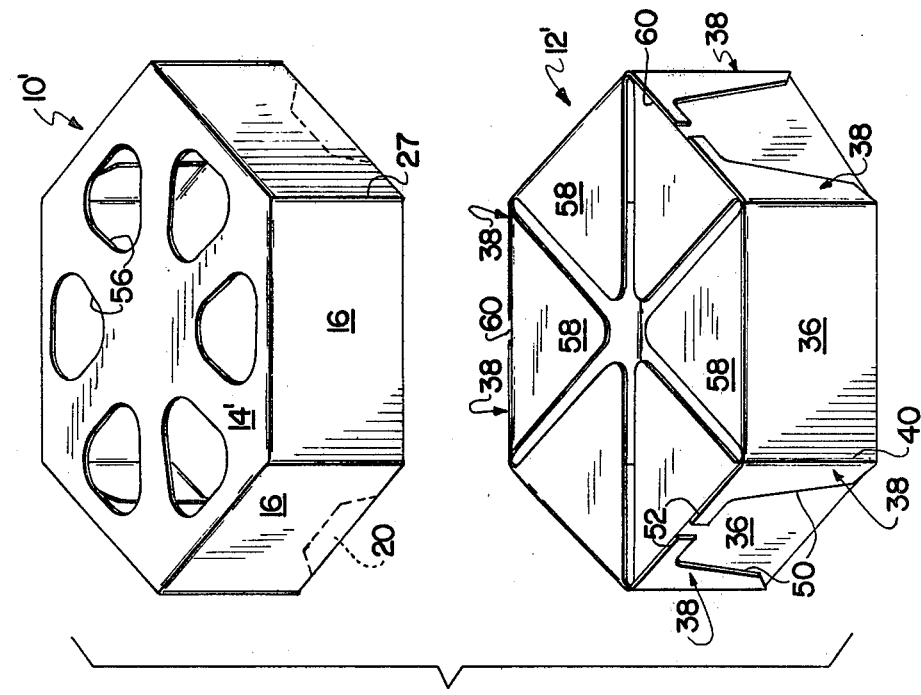
FIG. 12 is an exploded perspective view of the upper and lower units shown in FIGS. 10 and 11 set up to form the completed carton.
Figure 10:
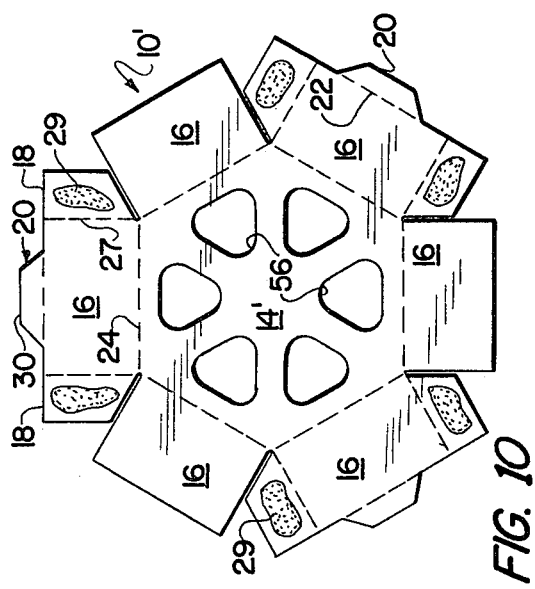
FIG. 10 is a top plan view of a modified blank in accordance with the present invention which is the same as that shown in FIG. 1 except that a plurality of openings are formed in the central panel thereof.
Figure 11:
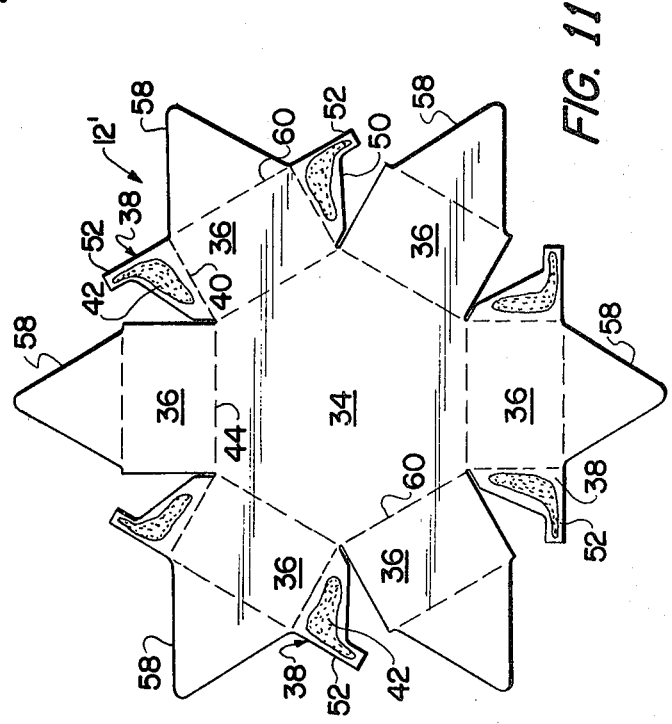
FIG. 11 is a top plan view of a modified lower unit blank in accordance with the present invention which is the same as the blank shown in FIG. 2 except that the rectangular panels do not have openings therein but do have triangular flaps extending from longitudinal edges thereof.

Embodiment Of FIGS. 10–12

The embodiment shown in FIGS. 10 and 11 of the present invention is particularly useful as an air freshener.

The upper unit 10' shown therein is the same as the upper unit shown in FIG. 1 except that six substantially equally spaced substantially triangular openings 56 are formed through the central panel 14'. The remaining parts of the upper unit 10' are the same as that shown in FIG. 1 and described above and are therefore given the same reference numerals.

As seen in FIG. 11, the modified lower unit 12' is the same as the lower unit 12 seen in FIG. 2 and described in detail above except there are no openings 46 on the side panels but each side panel 36 has a triangular flap 58 extending from the distal longitudinal edge thereof hingedly along a fold line 60. The remaining parts are the same as that shown in FIG. 2 and are given the same reference numerals.

As seen in FIG. 12, the modified upper and lower units 10' and 12' are set up substantially the same way as units 10 and 12 except that in addition the triangular flaps 58 are folded inwardly of the lower unit 12'. This folding is along fold line 60 and results in the triangular flaps 58 assuming a substantially parallel configuration to the bottom central panel 34 of the lower unit 12', as seen in FIG. 12.

As is evident from FIG. 12, the upper and lower units 10' and 12' are connected and slidably related as are units 10 and 12. As seen in FIG. 12, the openings 56 in the upper unit 10' overlie the central portion of the triangular flaps 59 so that air can flow through and into or out of the formed carton from units 10' and 12' via openings 56 and the spaces between the triangular flaps 58 oriented in a position shown in FIG. 12.

While various advantageous embodiments have been chosen to illustrate the invention, it will be understood by those skilled in the art that various changes and modifications can be made therein without departing from the scope of the invention as defined in the appended claims.

What is claimed is:
1. A paperboard carton comprising:
   (a) an upper unit including a regular polygonal top wall having a plurality of side walls with one of said side walls being coupled to and depending from each edge of said top wall;

(b) a lower unit telescopingly slidably movable in said upper unit along a common longitudinal axis, said lower unit including a regular polygonal bottom wall complimentary in shape to said top wall, said bottom wall having a plurality of side walls with one of said side walls being coupled to and depending from each edge of said bottom wall, said lower unit side walls being inwardly adjacent to said upper unit side walls;

(c) said upper unit being axially slidable with respect to said lower unit between a closed position and an open position;

(d) access means in at least one of said upper and lower units for opening the interior of said carton to ambient surroundings only when said upper unit is in said open position; and (e) cooperating locking means on said upper and said lower units to preclude complete removal of said upper unit from said lower unit when said upper unit is moved to said open position, said locking means comprising: a plurality of locking flaps hingedly coupled to distal edges of a plurality of said side walls of one of said upper and lower units, said locking flaps being folded against said side walls to provide a plurality of locking surfaces; and a plurality of stop tabs folded against comparable side walls on the other of said upper and lower units to provide a plurality of stop surfaces, said locking surfaces, and said stop surfaces being axially spaced apart when said upper unit is in said closed position, and said locking surfaces and said stop surfaces being in abutting contact when said upper unit is in said open position to preclude complete separation of said upper unit from said lower unit.

2. The carton of claim 1 wherein said stop tabs are foldably connected to the side walls of said lower unit adjacent to said comparable side walls.

3. The carton of claim 1, wherein said locking flaps are trapezoidal in configuration and are foldably connected to said distal edges of said side walls along basal fold lines which are shorter than the length of said distal edges.

4. A paperboard carton comprising:

(a) a first unit including a regular polygonal wall having a plurality of side walls with one of said side walls being coupled to and extending perpendicularly to each edge of said polygonal wall;

(b) trapezoidal locking flaps hingedly coupled along the larger base thereof to alternate ones of said first unit side walls at free edges thereof, said larger base of said locking flaps being shorter in length than the length of said free edges to which said locking flaps are coupled, and said locking flaps being folded against and secured to said alternate side walls to form locking surfaces;

(c) a second unit including a regular polygonal wall having a plurality of side walls with one of said side walls being coupled to and extending perpendicularly to each edge of said second unit polygonal wall;

(d) means forming trapezoidal stop surfaces on alternate ones of said second unit side walls;

(e) said first and second units being disposed in telescoping relationship for limited axial movement relative to each other between first and second positions, said trapezoidal locking flaps and said trapezoidal stop surfaces being spaced apart when said first and second units are in said first position, and being in abutting contact when said first and second units are in said second position to preclude complete separation of said first and second units; and (f) means forming a plurality of openings in the innermost of said first and second units with said openings being closed by the outermost unit when said first and second units are in said first position, and said openings being open to ambient surroundings when said first and second units are in said second position.

* * * * *